United States Patent [19]
Furuyoshi et al.

[11] Patent Number: 4,814,077
[45] Date of Patent: Mar. 21, 1989

[54] LIPOPROTEIN ADSORBENT AND APPARATUS FOR REMOVING LIPOPROTEINS USING THE SAME

[75] Inventors: Shigeo Furuyoshi, Kobe; Nobutaka Tani, Osaka, both of Japan

[73] Assignee: Kanegafuchi Kagaku Kogyo Kabushiki Kaisha, Osaka, Japan

[21] Appl. No.: 12,232

[22] Filed: Feb. 9, 1987

[30] Foreign Application Priority Data

Feb. 10, 1986 [JP] Japan .................. 61-27727

[51] Int. Cl.$^4$ ............................................ B01D 15/00
[52] U.S. Cl. .................. 210/266; 210/502.1; 210/679; 502/401
[58] Field of Search ............ 210/679, 263, 266, 502.1, 210/504, 506; 502/401

[56] References Cited

U.S. PATENT DOCUMENTS

| | | | |
|---|---|---|---|
| 3,755,161 | 8/1973 | Yokota et al. | 210/679 |
| 4,112,185 | 9/1978 | Meiller | 428/403 |
| 4,308,254 | 12/1981 | Tayot et al. | 424/124 |
| 4,321,136 | 3/1982 | Takiguchi et al. | 536/18 |
| 4,409,105 | 10/1983 | Hayashi et al. | 210/266 |

FOREIGN PATENT DOCUMENTS

| 0154315 | 9/1985 | European Pat. Off. |
|---|---|---|
| 2092470 | 8/1982 | United Kingdom |

*Primary Examiner*—Ivars Cintins
*Attorney, Agent, or Firm*—Armstrong, Nikaido, Marmelstein & Kubovcik

[57] ABSTRACT

An adsorbent for lipoproteins which is a water-insoluble matrix having, on at least a part of the surface thereof, a group of the formula $-NR^1R^2$ wherein $R^1$ is hydrogen, methyl group or ethyl group; $R^2$ is an atomic group having an aromatic ring satisfying that the value of log P, in which P is a distribution coefficient in a water-octanol system, of a compound of the formula $R^2H$ is from 0 to 3.2 and an apparatus for removing lipoproteins using the above adsorbent. The lipoprotein adsorbent has such advantages as a low cost, a good stability and a sufficient adsorption selectivity for adsorbing LDL and VLDL in a fluid containing lipoproteins.

6 Claims, 2 Drawing Sheets

LIPOPROTEIN ADSORBENT AND APPARATUS FOR REMOVING LIPOPROTEINS USING THE SAME

BACKGROUND OF THE INVENTION

The present invention relates to an adsorbent for removing lipoproteins in blood and the like, more specifically an adsorbent for selectively adsorbing lipoproteins containing apo-B-protein, i.e. low density lipoprotein (hereinafter referred to as "LDL") and very low density lipoprotein (hereinafter referred to as "VLDL") and to an apparatus for removing lipoproteins.

It has been known that lipoproteins present in blood, especially LDL and VLDL, contain a large amount of cholesterol and cause arteriosclerosis. On the other hand, it has been known that high density lipoprotein (hereinafter referred to as "HDL") is a factor which delays causing arteriosclerosis.

As a method for removing LDL and VLDL from body fluid such as blood, there has been employed methods using a membrane and using an adsorbent. In the above method using a membrane, a fair amount of HDL are removed as well as LDL and VLDL. Thus it does not satisfy the desired selectivity of lipoprotein. Further, since some plasma proteins are removed at the same time, it is necessary to supply plasma proteins.

With regard to methods using an adsorbent, there are, for instance, a method using an adsorbent wherein an antibody is immobilized, so-called immunoadsorbent, and a method using an adsorbent based on the principle of the affinity chromatography, wherein a compound having an affinity for LDL and VLDL (such compound is hereinafter referred to as "ligand") is immobilized.

Though the method using an immunoadsorbent provides an almost sufficient selectivity, there are many problems such as difficulty for obtaining the antibody, a high price of the antibody, poor stability of the adsorbent when preserving.

In the method based on the principle of affinity chromatography, heparin, dextran sulfate and the like are typically used as a ligand. The adsorbent immobilized with the above ligand has a good selectivity and the ligand employed is not too expensive. However, many of them are difficult to sterilize and it is required to lower the cost for using ligands in large quantities.

There is also an adsorbent, which has an organic compound such as phenylglycidyl ether as a ligand, adsorbing lipoproteins by hydrophobic interaction between phenyl group and the hydrophobic part on the surface of a lipoprotein. As the above adsorbent, there is commercially available Phenyl-Sepharose CL-4B (made by Pharmacia Fine Chemicals AB). While this adsorbent is inexpensive, it has a serious problem in selectivity as it adsorbs not only LDL and VLDL but also large amount of HDL.

The object of the present invention is to provide a low-cost and stable adsorbent which can selectively remove LDL and VLDL from the body fluid.

The present invention relates to an adsorbent for lipoproteins which is a water-insoluble matrix having, on at least a part of the surface thereof, a group of the formula:

$$-NR^1R^2$$

wherein $R^1$ is hydrogen, methyl group or ethyl group; and $R^2$ is a substituent with an aromatic ring and satisfying the condition that the value of log P, in which P is a partition coefficient in a water-octanol system, of a compound of the formula $R^2$

$$P = \frac{[R^2H] \text{ octanol}}{[R^2H] \text{ water}}$$

is from 0 to 3.2.

The present invention relates to an apparatus for removing lipoproteins which comprises a container having a fluid inlet and a fluid outlet, filters through which a fluid and components included in the fluid can pass while an adsorbent, which is the above mentioned water-insoluble matrix, cannot pass, and which are provided at both the inlet and outlet, and an adsorbent which is packed in the container.

DETAILED DESCRIPTION OF THE INVENTION

Figure 1:
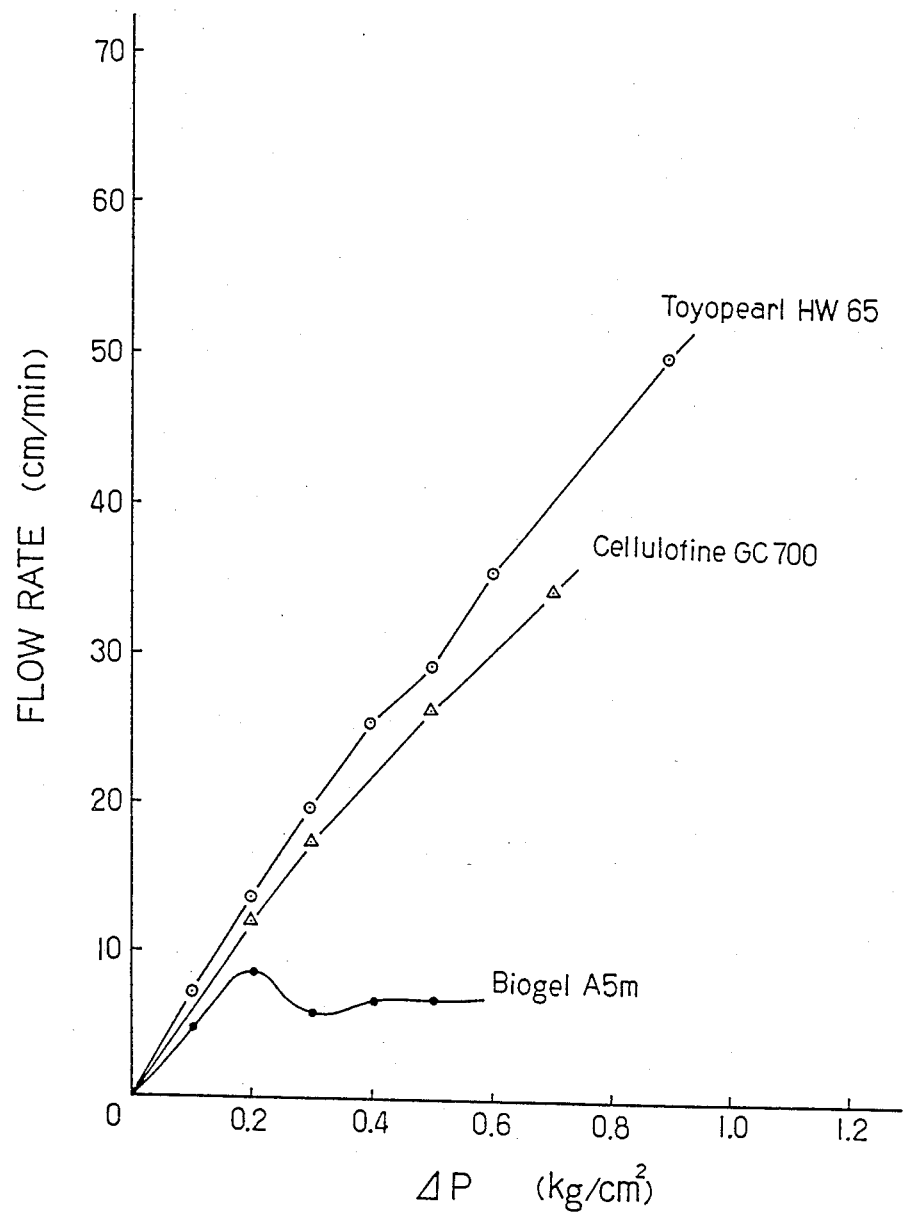
FIG. 1 is a graph showning a relation between a flow rate and a pressure drop $\Delta P$ obtained in Reference Example.

As a result of making a study of various water-insoluble matrices having various atomic groups prepared with paying attention to the hydrophobic and electrostatic interaction, which are the most important interactions among physico-chemical interactions between proteins and ligands, it has now been found that the water-insoluble matrix having, on the surface, a group of the formula:

$$-NR^1R^2$$

wherein $R^1$ is hydrogen, methyl group or ethyl group; and $R^2$ is a substituent with an aromatic ring and satisfying that the value of log P, wherein P is a distribution coefficient in a water-octanol system, of a compound of the formula $R^2H$ formula

$$P = \frac{[R^2H] \text{ octanol}}{[R^2H] \text{ water}}$$

is from 0 to 3.2 adsorbs LDL and VLDL but hardly adsorbs any HDL.

As a result of comparing the adsorbent, wherein $R^1$ of $-NR^1R^2$ is hydrogen atom and $R^2$ is phenyl group, of the present invention with the adsorbent having $-O-$ instead of $-NR^1-$ in the above adsorbent, it has been found that the latter adsorbs not only both LDL and VLDL but also a lot of HDL at the same time as against that the former adsorbs LDL and VLDL, hardly any HDL. Consequently, nitrogen atom is critical to the selectivity of adsorption between the LD- and VLD-lipoproteins and the HD-lipoprotein and is an important constituent atom in the structure of this adsorbent.

On the other hand, it is important that $-R^2$, which exists in the group $-NR^1R^2$ of the adsorbent of the present invention, is aromatic. The reason is based on the fact that as a result of comparing two adsorbents with each other, provided both adsorbents have a group $-NR^1R^2$ wherein both of $R^1$ are hydrogen atom; $R^2$ is phenyl group and butyl group respectively, the value of log P of a compound of the formula $R^2H$ in the above two cases are almost the same, the latter is much inferior to the former in the capacity for adsorbing LDL. This is why an aromatic ring critical to the affinity for LDL.

The typical examples of the preferable aromatic ring to be included in the atomic group $R^2$ of $-NR^1R^2$ existing in the adsorbent of the present invention, are benzene, pyridine, pyrimidine, triazine, pyrrol, imidazol, furan, thiophene, a condensed ring of them and the like. However, the present invention is not limited thereto.

The logarithm of a distribution coefficient in water-octanol system, i.e. log P, is a hydrophobic parameter of a compound. The distribution coefficient P is obtained according to the following typical method.

First of all, a compound is dissolved in an octanol (or a water) and an equal volume of a water (or an octanol) is added thereto. After shaking for 30 minutes by Griffin flask shaker (made by Griffin and Jorge Ltd.), it is centrifuged for from 1 to 2 hours at 2000 rpm. Then concentrations of the compound in both octanol and water layer can be measured by various methods such as spectroscopic method and GLC and P is obtained according to the following formula:

$$P = \frac{[R^2H] \text{ octanol}}{[R^2H] \text{ water}}$$

Coct: a concentration of a compound in an octanol layer

Cw: a concentration of a compound in a water layer

The hydrophobic property of the atomic group $-R^2$ of the group $-NR^1R^2$ existing in the adsorbent of the present invention, plays an important role in a bond between the adsorbent and lipoprotein.

In case that the value of log P of $R^2H$ is less than 0, a hydrophobic interaction with lipoproteins is so weak that a capacity for adsorption of lipoproteins is low. On the contrary, in case that the value of log P is more than 3.2, there is a problem in point of selectivity because not only LDL but also HDL and any other proteins are adsorbed. Therefore, the value of log P of a compound of the formula $R^2H$ wherein $R^2$ is an atomic group in the adsorbent of the present invention is from 0 to 3.2, preferably from 0.8 to 2.7.

The typical examples of the compound of $R^2H$ satisfying that the value of log P of a compound of the formula $R^2H$ is from 0 to 3.2, are, in case that an aromatic ring is a benzene ring, benzene, toluene, xylene, ethylbenzene, phenol, benzyl alcohol, phenethyl alcohol, benzaldehyde, anisole, phenetole, benzoic acid, phenyl acetate, phenoxy acetate, methyl benzoic acid, aniline, nitrobenzene, chlorobenzene, dinitrobenzene, nitrobenzaldehyde, nitroanisole, nitrotoluene, benzamide, acetophenone, ethylphenol, ethoxyphenol, acetanilide, phenylacetamide, methylbenzyl alcohol and so on. However, the present invention is not limited thereto. The atomic group $R^2$ including other aromatic rings satisfying that the value of log P of $R^2H$ is from 0 to 3.2, also can be used without any particular limitation.

Moreover, the group $-NR^1R^2$ which is existing on at least a part of the surface of a water-insoluble matrix of the present invention, can be employed one or more kinds.

The adsorbent, which is characterized by being a water-insoluble matrix of the present invention and having, on at least a part of the surface of the matrix, the group $-NR^1R^2$ wherein $R^1$ is hydrogen atom, methyl group or ethyl group; $R^2$ is an atomic group having an aromatic ring and satisfying that the value of log P, in which P is a distribution coefficient in a water-octanol system, of a compound of the formula $R^2H$ is from 0 to 3.2 is distinguished according to the process for preparation as described below. Both of them can be adaptable to the present invention.

(1) The adsorbent obtained by introducing the group $-NR^1R^2$ into a water-insoluble carrier.

(2) The adsorbent obtained by introducing the group $-NR^1R^2$ into a water-soluble high molecular weight compound, and then subjecting them a treatment such as cross-linking to give a water insoluble matrix.

The water-insoluble carrier used for the adsorbent in the above process (1) can be an inorganic carrier, an organic carrier consisting of synthetic high molecular compound or polysaccharide, and a complex carrier consisting of organic carrier and/or inorganic carrier. It is preferable that the carrier has hydrophilic property from the point of the environment of lipoproteins existing in body fluid and have little adsorption for the materials except the object materials, so-called non-specific adsorption.

Typical examples of the above water-insoluble carrier are a water-insoluble carrier consisting of polysaccharides such as cross-linked agarose, cross-linked dextran, cross-linked cellulose, crystalline cellulose, cross-linked chitin and cross-linked chitosan, a water-insoluble carrier consisting of synthetic high molecular compound such as cross-linked polyvinylalcohol, cross-linked polyacrylate and cross-linked polyamide, inorganic carriers such as glass beads and silica gel, organic-inorganic complex carrier which the surface of inorganic carrier are coated with polysaccharides or high molecular compound, organic-organic complex carrier which the surface of organic carrier consisting of synthetic high molecular compound are coated with polysaccharides and the like. However, the present invention is not limited thereto.

Typical examples of water-soluble high molecular compound used for preparation of the adsorbent in the above process (2) are polysaccharides such as dextran and starch, high molecular compound such as polyvinyl alcohol and saponificating product of ethylenevinyl acetate copolymer having a small content of ethylene. However, the present invention is not limited thereto.

During the process for preparation of both adsorbents of the above process (1) and (2), the group $-NR^1R^2$ is introduced into a water-insoluble carrier or a water-soluble high molecular compound. In the present invention, it is preferable that the group $-NR^1R^2$ is immobilized onto a water-insoluble carrier or a water-soluble high molecular compound by a covalent bond because of a small possibility of release of ligands. Therefore, it is more preferable that there are some functional groups, which are available for immobilizing reaction, on a water-insoluble carrier or a water-soluble high molecular compound used for the adsorbent of the present invention.

Typical examples of the above functional groups are amino group, carboxyl group, hydroxyl group, thiol group, aldehyde group, halogen group, acid anhydride group, amide group, ester group, epoxy group, silanol group and the like.

The nitrogen atom existing in the group $-NR^1R^2$ in the adsorbent of the present invention, which is supporsed to be concerned with the selectivity of adsorption between the LD- and VLD-lipoproteins and the HD-lipoprotein, can be derived from either a water-insoluble carrier, a water-soluble high molecular compound or a ligand.

In other words, there are some methods to introduce a group $-NR^1R^2$ into either a water-insoluble carrier or a water-soluble carrier; one is that the group $-NR^1R^2$ is a group derived from a compound of the formula $HNR^1R^2$, wherein $R^1$ and $R^2$ are as defined above, and immobilized to a water-insoluble carrier via amino group of the compound and another is that the group $-NR^1R^2$ is combined with the carrier by reacting a water-insoluble carrier having a group of the formula $-NHR^1$, wherein $R^1$ is as defined above, with a compound of the formula $R^2X$, wherein $R^2$ is as defined above and X is a functional group capable of reacting with amino group or a part of the functional group. Both of them are available in the present invention.

The term "a carrier having amino group" in the above is a carrier consisting of a material originally having amino group such as chitin and chitosan, or a carrier at first prepared by introducing amino group into a carrier originally having no amino group by being activated with cyanogen bromide, epichlorohydrine, 1,4-butanediol diglycidyl ether and the like and then being reacted with the compound of either $H_2NR^1$ or $HNR^1R^3$ wherein $R^3$ is an atomic group having a functional group capable of binding to a carrier.

When the group $-NR^1R^2$ is introduced into a water-insoluble carrier or a water-soluble high molecular compound, in case of combining the compound $HNR^1R^2$ with the carrier, aniline, aniline derivative, a mixture of aniline and aniline derivative, benzylamine, benzylamine derivative and a mixture of benzylamine and benzylamine derivative are particularly useful as a compound of $HNR^1R^2$. Examples of aniline derivative are N-monoalkylanilines such as N-methylaniline and N-ethyl-aniline; aromatic alkyl-substituted anilines such as o-toluidine, m-toluidine, p-toluidine, 2,3-xylidine and 2,4-xylidine; aromatic alkoxysubstituted-anilines such as o-aminoanisole, m-aminoanisole, 2-aminophenetole, 3-aminophenetole and 4-aminophenetole; anilines having one or more substituent group consisting of one or more kinds of substituent groups on the aromatic ring, for instance, o-chloroaniline, m-chloroaniline, p-chloroaniline, o-nitroaniline, m-nitroaniline, p-nitroaniline, 2,4-dinitroaniline, 2,6-dinitroaniline, 3,5-dinitroaniline, o-aminobenzoic acid, m-aminobenzoic acid, p-aminobenzoic acid, o-ethyl aminobenzoate, m-ethyl aminobenzoate, p-ethyl aminobenzoate, p-aminobenzensulfonamide, o-aminophenol, m-aminophenol, p-aminophenol, o-aminophenethyl alcohol, p-aminophenethyl alcohol, o-phenylenediamine, m-phenylenediamine, p-phenylenediamine, 2-amino-4-nitroanisole, 2-amino-4-nitrotoluene and the like. The present invention is not limited thereto.

The adsorbent of the present invention can be employed in order to remove LDL and VLDL from blood, serum, plasma, a diluted solution of blood, serum or plasma and a solution containing various lipoproteins, for instance, a solution which has been subjected to a pretreatment such as removal of blood cells, and/or serum proteins.

Typically, the adsorbent of the present invention can be used as a adsorbent for treating patiants of hyperlipemia or a adsorbent for analyzing various lipoproteins.

The adsorbent of the present invention can be used for therapy in various ways.

For the most simple example, the adsorbent of the present invention can be used as follows: i.e. patient's blood is introduced outside of his body so as to be put into a blood bag and then mixed with the adsorbent of the present invention to remove LDL and VLDL, followed by removing the adsorbent through filteration. Consequently, the blood treated in this way is returned back to the patient himself. Though this method does not need an intricate apparatus, there are some defects such as a small amount of a treated blood at one time, a lot of time of therapy and a complicated operation.

For another method, a column packed with the adsorbent of the present invention is incorporated into an extracorporeal circulation circuit, and then removal of LDL and VLDL by adsorption is taken by on-line system. There are two treatment methods. One is that whole blood is directly perfused and another is that only plasma separated from the blood is passed through the column.

Both the adsorbent and the apparatus for removing lipoproteins of the present invention can be used in any of the above-mentioned methods.

The apparatus for removing lipoproteins of the present invention comprises a container having a fluid inlet and a fluid outlet, filters through which a fluid and components included in the fluid can pass while the adsorbent packed in cannot pass and which are provided at both the above inlet and outlet and, the adsorbent of the present invention is packed in the above container. A schematic longitudinal sectional view of the example of the apparatus for removing lipoprotains is shown in FIG. 2.

Figure 2:
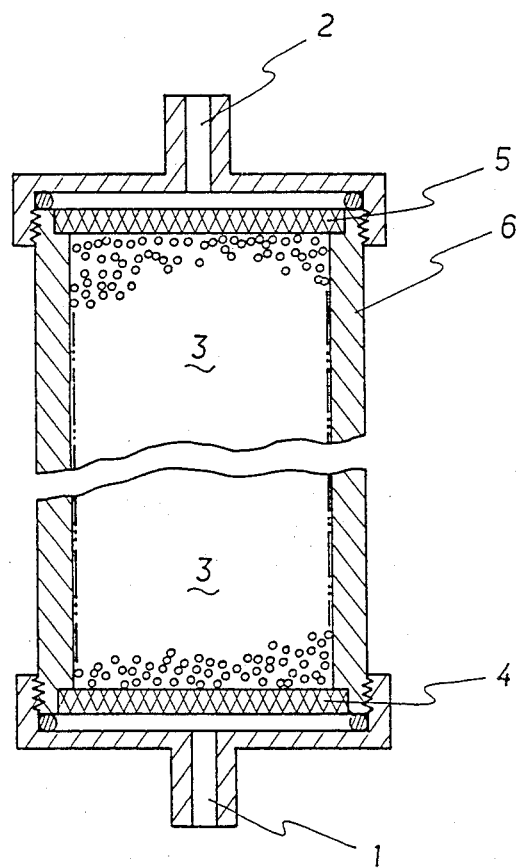
FIG. 2 is a schematic longitudinal sectional view of an example of apparatus for removing lipoproteins.

In FIG. 2, 1 and 2 are a fluid inlet and a fluid outlet respectively, 3 is the adsorbent of the present invention, 4 and 5 are filters or mesh which the fluid and components thereof can pass through while the adsorbent can not pass through, and 6 is a column. The filter 4 of the fluid inlet side may be excepted.

It is preferable that the adsorbent has a sufficient mechanical strength, i.e. hard adsorbent, so as to prevent compaction of the adsorbent during filling a column with the adsorbent, incorporating the column into an extracorporeal circulation circuit, and treating patients with it by on-line system.

The structure of the adsorbent of the present invention can be porous or non-porous. Especially, it is preferable that the specific surface area is large, that is to say, the adsorbent has a porous structure, particularly a whole porous structure, in order to get a high capacity for adsorbing LDL per unit volume of the adsorbent.

The term "hard" in the present invention means, as shown in the Reference Example herein below, that the relation between a pressure drop and a flow rate determined by passing an aqueous fluid through a cylindrical column uniformly filled with the waterinsoluble matrix keeps a linear relationship until the pressure drop is increased to 0.3 kg/cm$^2$, which is the minimum required mechanical strength of the adsorbent for incorporating the column into an extracorporeal circulation circuit.

The term "porous structure" means that the volume of the pore of the adsorbent is not less than 20% and a specific surface area of it is not less than 3 m$^2$/g. Otherwise, the adsorbent capacity becomes too small. Typical examples of the above mentioned carrier are porous cellulose gel, porous chitosan gel, vinyl porous carrier such as styrene-divinylbenzene copolymer, cross-linked acrylate, cross-linked polyvinyl alcohol, inorganic porous carrier such as glass, silica, alumina. The present invenion is not limited thereto.

In case that the adsorbent of the present invention has a porous structure, it is important that there is such a pore size as LDL and VLDL, which have not less than $1 \times 10^6$ of molecular weight, can easily enter in it. It means that the molecular weight of the exclusion limit measured with globular proteins is not less than $1 \times 10^6$. The molecular weight of the exclusion limit under $1 \times 10^6$ has so small capacity of adsorption that it is not suitable for practical use. On the other hand, the molecular weight of the exclusion limit over $1 \times 10^8$ is not suitable for practical use either because the mechanical strength is weakened and the amount of solid contained in the adsorbent is too small to get the sufficient capacity for the adsorption. Therefore, the preferable molecular weight of the exclusion limit of an adsorbent of the present invention is from $10^6$ to $10^8$ More preferably, the exclusion limit is $3 \times 10^6$ to $7 \times 10^7$ from the points of rather free permeation of proteins to be adsorbed, the strength of the adsorbent and the adsorbent capacity.

The term "the molecular weight of the exclusion limit" means, for instance, as described in the literature such as "Jikken Kosoku Ekitai Chromatography (Experimental High Speed Liquid Chromatography)", Hiroyuki Hatano and Toshihiko Hanai, published by Kabushiki Kaisha Kagaku Dojin, the minimum molecular weight of the molecule which cannot permeate into a pore, i.e. which is excluded, in a gel permeation chromatography.

The shape of an adsorbent of the present invention can be optionally selected from shape such as particle, fiber, sheet and hollow fiber.

The present invention is more specifically described and explained by the following Reference Example, Examples and Comparative Examples. It is to be understood that the present invention is not limited to the Reference Example, Examples and Comparative Examples and various changes and modifications can be made without departing from the scope and spirit of the present invention.

REFERENCE EXAMPLE

A relation between a flow rate and a pressure drop was determined by passing water by means of a peristaltic pump through cylindrical glass columns equipped at both ends with filters having a pore size of 15 μm (inner diameter: 9 mm, column length: 150 mm), in which an agarose gel (Biogel A5m made by Biorad Co., particle size: 50 to 100 mesh) and hard gels made of a polymer (Toyopearl HW 65 made by Toyo Soda Manufacturing Co., Ltd., particle size: 50 to 100 μm, and Cellulofine GC-700 made by Chisso Corporation, particle size: 45 to 105 μm) were packed respectively. The results are shown in FIG. 1.

As shown in FIG. 1, an increase of a flow rate is nearly proportional to that of a pressure drop in case of hard gels made of a polymer, whereas in case of an agarose gel, consolidation occurrs and a flow rate does not increase even if a pressure drop increases.

EXAMPLE 1

Twenty ml of n-heptane, 6 ml of a 20% by weight aqueous solution of sodium hydroxide and 2 drops (50 μl) of Tween 20 (made by Kao Atlas Kabushiki Kaisha) were added to 20 ml of a porous cellulose gel (CK gel A-3 made by Chisso Corporation, exclusion limit of globular protains: $5 \times 10^7$, particle size: 63 to 125 μm). After stirring for 2 hours at 40° C., there was added 6 ml of epichlorohydrin. Further, after the stirring was continued for 2 hours a 40° C. and then washed with water, an epoxy-activated gel was obtained. To 10 ml of the obtained epoxide epoxy-activated gel, 10 ml of a 30% by volume aqueous solution of dioxane wherein 300 mg of aniline was dissolved was added. After 4 hours reaction by allowing it to stand at 40°, the resultant gel was filtered and washed with a 15% by volume aqueous solution of dioxane, water, a 2M aqueous solution of sodium chloride and water in turn to obtain an aniline-immobilized gel.

One ml of the obtained aniline-immobilized gel was put into a test tube, and thereto 4 ml of human serum was added. After shaking for 2 hours at 37° C., the concentrations of LDL, VLDL and HDL-cholesterol in the supernatant liquid were measured. The result is shown in Table 1.

EXAMPLE 2

There was suspended 20 ml of a cross-linked agarose gel (Sepharose CL-6B made by Pharmacia Fine Chemicals AB, exclusion limit: $4 \times 10^6$, particle size: 45 to 165 μm) to 20 ml of water.

And there was added 10 ml of a 2M aqueous solution of sodium hydroxide and adjusted at 40° C. Then thereto 4 ml of epichlorohydrin was added. After stirring for 2 hours at 40° C. and then washing with water, an epoxy-activated gel was obtained. To 10 ml of the obtained epoxy-activated gel, 10 ml of a 30% by volume aqueous solution of dioxane wherein 300 mg of aniline was dissolved was added. After 4 days reaction by allowing it to stand at room temperature, the resultant gel was filtered and washed with a 15% by volume aqueous solution of dioxane, water, a 2M aqueous solution of sodium chloride and water in turn to obtain an aniline-immobilized gel.

One ml of the obtained aniline-immobilized gel was put into a test tube, and thereto 4 ml of human serum was added. After shaking for 2 hours at 37° C. the concentrations of LDL, VLDL and HDL-cholesterol in the supernatant liquid were measured. The result is shown in Table 1.

EXAMPLE 3

There was added 10 ml of water, 5.4 ml of a 2M aqueous solution of sodium hydroxide and 1.9 ml of epichlorohydrin to 10 ml of a porous cellulose gel (CK gel A-3 made by Chisso Corporation, exclusion limit of globular protains: $5 \times 10^7$, particle size: 63 to 125 μm). After completion of the reaction under stirring for 2 hours at 40° C., the resultant gel was filtered and washed with water to obtain an epoxy-activated gel. To 10 ml of the obtained epoxy-activated gel, 8 ml of water and 137 mg of benzylamine were added. After mixing well, the mixture was allowed to stand for 6 days at 50° C. After completion of the reaction, the resultant gel was filtered and then washed with water to obtain a benzylamine-immobilized gel.

One ml of the obtained benzylamine-immobilized gel was put into a test tube, and thereto 4 ml of human serum was added. After shaking for 2 hours at 37° C., the concentrations of β-lipoprotein and HDL-cholesterol in the supernatant liquid were measured. The result is shown in Table 2.

EXAMPLE 4

The procedure of Example 3 were repeated except that 120 mg of aniline was used instead of 137 mg of benzylamine in Example 3 to obtain an aniline-immobilized gel and examine the absorption of the obtained aniline-immobilized gel. The result is shown in Table 2.

EXAMPLE 5

There was added 10 ml of water and 0.5 ml of a 30% aqueous ammonium solution to 10 ml of epoxy-activated CK gel A-3 obtained by the same procedures as in Example 3. After mixing well, the mixture was allowed to stand for 2 days at 40° C. After completion of the reaction, the resultant gel was filtered and then washed with water to obtain an aminated gel (hereinafter referred to an N-gel). 10 ml of the obtained N-gel was washed with 50 ml of dioxane, 50 ml of a 10% by volume triethylamine dioxane solution and 100 ml of dioxane in turn on a glass filter. Then the gel was transferred to a reaction vessel, and thereto 25 ml of dioxane wherein 90 mg of benzoic acid was dissolved. 2 ml of dioxane wherein 100 mg of dicyclohexyl carbodiimide was dissolved was added under stirring. After the stirring was continued for 3 hours, there was further added 2 ml of dioxane wherein 100 mg of dicyclohexyl carbodiimide was dissolved was added. After completion of the reaction under stirring for 3 hours, the resultant gel was filtered and then washed with 100 ml of dioxane, 100 ml of methanol, 100 ml of dioxane and 500 ml of water in turn to obtain a benzoic acid-immobilized N-gel.

One ml of the obtained benzoid acid-immobilized gel was put into a test tube, and thereto 4 ml of human serum was added. After shaking for 2 hours at 37° C., the concentrations of $\beta$-lipoprotain and HDL-cholesterol in the supernatant liquid were measured. The result is shown in Table 2.

EXAMPLE 6

The procedures of Example 5 were repeated except that 123 mg of p-nitrobenzoic acid was used instead of 90 mg of benzoic acid to give a p-nitrobenzoic acid-immobilized N-cellulose gel and examine the absorption of the obtained p-nitrobenzoic acid-immobilized N-cellulose gel. The result is shown in Table 2.

EXAMPLE 7

The procedures of Example 3 were repeated except that 155 mg of phenethylamine was used instead of 137 g of benzylamine and that 10 ml of a 30% by volume aqueous solution of dioxane was used instead of 10 ml of water to obtain a phenethylamine-immobilized gel and examine the adsorption of the obtained phenethylamine-immobilized gel. The result is shown in Table 2.

EXAMPLE 8

The procedures of Example 3 were repeated except that p-aminobenzenesulfonamide was used instead of benzylamine to obtain a p-aminobenzensulfonamide immobilized gel and examine the adsorption of the obtained p-aminobenzensulfonamide-immobilized gel. The result is shown in Table 2.

COMPARATIVE EXAMPLE 1

One ml of Phenyl-Sepharose CL-4B (made by Pharmacia Fine Chemicals AB) was put into a test tube, and thereto 4 ml of human serum was added. After shaking for 2 hours at 37° C., the concentrations of LDL, VLDL and HDL-cholesterol in the supernatant liquid were measured. The result is shown in Table 1.

COMPARATIVE EXAMPLE 2

One ml of Ringer's solution (made by Otsuka Seiyaku Kabushiki Kaisha) was put into a test tube, and thereto 4 ml of human serum was added. After shaking for 2 hours at 37° C., the concentrations of LDL, VLDL and HDL-cholesterol in the supernatant liquid were measured. The result is shown in Table 1.

COMPARATIVE EXAMPLE 3

The procedures of Example 3 were repeated except that 94 mg of n-butylamine was used instead of 137 g of benzylamine to obtain a n-butylamine-immobilized gel and examine the adsorption of the obtained n-butylamine-immobilized gel. The result is shown in Table 2.

COMPARATIVE EXAMPLE 4

The procedures of Example 7 were repeated except that 173 mg of $\gamma$-phenylpropylamine was used instead of 155 g phenethylamine to obtain a $\gamma$-phenyl propylamine-immobilized gel and examine the adsorption of the obtained $\gamma$-phenylpropylamine-immobilized gel. The result is shown in Table 2.

COMPARATIVE EXAMPLE 5

One ml of Ringer's solution (made by Otsuka Seiyaku Kabushiki Kaisha) was put into a test tube, and thereto 4 ml of human serum was added. After shaking for 2 hours at 37° C., the concentration of $\beta$-lipoprotain and HDL-cholesterol in the supernatant liquid were measured. The result is shown in Table 2.

TABLE 1

| Example No. or Comparative Example No. | LDL (mg/dl) | VLDL (mg/dl) | HDL-cholesterol (mg/dl) |
| --- | --- | --- | --- |
| Ex. 1 | 65 | 41 | 42 |
| Ex. 2 | 140 | 71 | 42 |
| Com. Ex. 1 | 45 | 70 | 1 |
| Com. Ex. 2 | 367 | 111 | 42 |

TABLE 2

| Example No. or Comparative Example No. | $R^2H$ logP | $\beta$-lipoprotein (mg/dl) | HDL-cholesterol (mg/dl) |
| --- | --- | --- | --- |
| Ex. 3 | 2.7 | 106 | 38 |
| Ex. 4 | 2.1 | 100 | 37 |
| Ex. 5 | 1.5 | 184 | 38 |
| Ex. 6 | 1.9 | 124 | 38 |
| Ex. 7 | 3.2 | 85 | 35 |
| Ex. 8 | 0.3 | 224 | 38 |
| Com. Ex. 3 | 2.5 | 252 | 38 |
| Com. Ex. 4 | 3.6 | 54 | 8 |
| Com. Ex. 5 | — | 394 | 38 |

As shown in Table 1 and 2, the adsorbent of the present invention adsorbs both LDL and VLDL, while HLD-cholesterol is hardly adsorbed.

In addition to the ingredients used in the Examples, other ingredients can be used in the Examples as set forth in the specification to obtain substantially the same results.

What is claimed is:

1. An adsorbent for lipoprotein which is a water-insoluble matrix, in which a group of the formula:

$$-NR^1R^2$$

wherein $R^1$ is a hydrogen atom, methyl group or ethyl group; and $R^2$ is a substituent with an aromatic ring and satisfying the condition that the value of log P, in which P is a partition coefficeint for a compound of the formula $R^2H$ in a water-octanal system defined by the formula $$P = \frac{[R^2H] \text{ octanol}}{[R^2H] \text{ water}}$$

is from 0 to 3.2 and is immobilized onto at least a part of the surface thereof by a covalent bond.

2. The adsorbent of claim 1, wherein said water-insoluble matrix has a porous structure.

3. The adsorbent of claim 2, wherein said water-insoluble matrix has a pore size which excludes globular proteins having a molecular weight greater than between $1 \times 10^6$ to $1 \times 10^8$.

4. An absorbent for lipoprotein according to claim 1, wherein the compound of the formula $-NR^1R^2$ is anilino, an anilino derivitive, or a mixture thereof.

5. An absorbent for lipoprotein according to claim 1, wherein the compound of the formula $-NR^1R^2$ is a benzylamino, a benzylamino derivative, or a mixture thereof.

6. An apparatus for removing lipoprotein from body fluids comprising a container having at least one fluid inlet, at least one fluid outlet, filters at each inlet and outlet, and packed with a water-insoluble matrix,
    said filters being permeable to said body fluids and impermeable to said water-insoluble matrix,
    said water-insoluble matrix comprising an absorbent for lipoproteins in which a group of the formula:

$$-NR^1R^2$$

wherein $R^1$ is selected from the group consisting of hydrogen, methyl and ethyl, and $R^2$ is a substituent with an aromatic ring and satisfies the condition that the value of log P, wherein P is the partition coefficient for a compound of the formula $R^2H$ in a water-octanol system defined by the formula:

$$P = \frac{[R^2H] \text{ octanol}}{[R^2H] \text{ water}}$$

is from 0 to 3.2 and is immobilized onto at least a part of the surface thereof by a covalent bond.

* * * * *